United States Patent [19]
Bednarczyk et al.

[11] Patent Number: 5,777,278
[45] Date of Patent: Jul. 7, 1998

[54] MULTI-PHASE FLUID FLOW MEASUREMENT

[75] Inventors: Adam Bednarczyk, Carrollton; Robert E. Maute, Richardson; Laird B. Thompson, Dallas, all of Tex.

[73] Assignee: Mobil Oil Corporation, Fairfax, Va.

[21] Appl. No.: 764,404

[22] Filed: Dec. 11, 1996

[51] Int. Cl.$^6$ ...................................................... G01V 1/40
[52] U.S. Cl. .................... 181/102; 73/152.32; 73/19.03; 73/861.25; 73/861.28; 175/48; 166/264
[58] Field of Search ............................ 73/152.32, 19.03, 73/19.04, 861.19, 861.25, 861.31, 861.28; 175/48; 166/264; 181/102

[56] References Cited

U.S. PATENT DOCUMENTS

| | | | |
|---|---|---|---|
| 4,208,906 | 6/1980 | Roberts, Jr. | 73/155 |
| 4,433,573 | 2/1984 | Hulin | 73/155 |
| 4,452,077 | 6/1984 | Siegfried, II | 73/155 |
| 4,480,485 | 11/1984 | Bradshaw et al. | 73/861.28 |
| 4,571,693 | 2/1986 | Birchak et al. | 364/509 |
| 4,947,683 | 8/1990 | Minear et al. | 73/155 |
| 5,001,676 | 3/1991 | Broding | 367/31 |
| 5,035,147 | 7/1991 | Woodward | 73/861 |
| 5,092,167 | 3/1992 | Finley et al. | 73/155 |
| 5,113,867 | 5/1992 | Janszen | 128/661.04 |

OTHER PUBLICATIONS

Branagan, Paul et al., Tests Show Production Logging Problems in Horizontal Gas Wells, Jan. 10, 1994, Oil & Gas Journal, pp. 41–45.

Hill, A. D. et al., Production Logging Tool Behavior in Two–Phase Inclined Flow, Oct. 1982 Jrnl. of Pet Tech., pp. 2432–2440.

Kelman, J. S., Biphasic Fluid Studies for Production Logging in Large–Diameter Deviated Wells, Nov. '93, The Log Analyst pp. 6–10.

Ding, Z. X., A Comparison of Predictive Oil/Water Holdup Models for Production Log Interpretation in Vertical and Deviated Wellbores, Jun. 19–22, 1994, SPWLA Logging Symposium, pp. 1–18.

Zhu, Ding et al., The Effect of Flow from Perforations on Two–Flow: Implications for Production Logging, Oct. '88, Society of Petroleum Engineers, pp. 267–275.

*Primary Examiner*—J. Woodrow Eldred
*Attorney, Agent, or Firm*—Malcolm D. Keen

[57] ABSTRACT

A method and apparatus is disclosed to identify fluid hydrocarbon flow rates in a flow line such as a pipeline or a producing oil well having a unidirectional fluid flow including moving an acoustic tool through a flow line. Acoustic energy is transmitted into the fluid flow. The acoustic energy is then received when it is reflected back by interfaces within the fluid flow. The reflected acoustic energy is transformed into electrical signals. The electrical signals are rectified. The amplitude peaks of the rectified electrical signals are determined. The travel times of the amplitude peaks are also determined. The amplitude peaks and the time values are used to determine hydrocarbon gas and the hydrocarbon liquid in the hydrocarbon fluid flow in the oil well. A transducer within the acoustic tool rotates three hundred sixty degrees six times per second. This enables us to obtain holdup and velocities for the total flow around the tool even in non ideal operating conditions such as deviated wells.

17 Claims, 3 Drawing Sheets

MULTI-PHASE FLUID FLOW MEASUREMENT

BACKGROUND OF THE INVENTION

1. Field of the Invention

The present invention pertains to fluid flow measurement and more particularly to the measurement of fluid flow of one type of fluid within a second or more dissimilar fluid within a fluid flow line such as a cased wellbore or a hydrocarbon pipeline.

2. Related Prior Art

In the production of hydrocarbons from an oil well which connects an oil-bearing subsurface formation with the surface, it is often desirable to measure the fluid flow rate from the well. In other situations, where several wells contribute to a single flow line, it may be desireable to determine the composition of the contribution from each well or even the composition of the entire flow. The former may occur where the total flow contains an excess of gas and it may be required to determine which, if any, of the contributing wells is producing a high percentage of gas. Certain types of flow meters located on the surface of the earth have been used to carry out such a measurement in the past, generally by a sampling method or a method and apparatus that distinguishes liquid flow only. These methods and apparatus usually measure total liquid fluid flow, for example, water and oil.

One of the instruments which can be used to measure fluid flow is the borehole televiewer. This logging instrument includes a piezoelectric type or bender transducer. Acoustic pulses are transmitted from a rotating transducer to density change interfaces where they are reflected back to the transducer. The reflected waves are detected and further processed to determine various facets of the oil well in which the televiewer is operating.

Several methods for determining the percentage of flow for one fluid within another exist in the prior art. Some of these methods are illustrated in the following patents. Additional patents are included which demonstrate methods for gas determination.

U.S. Pat. No. 5,138,585, titled "Method For Fluid Identification And Evaluation Within Wellbores Using Ultrasonic Scanning", issued to Jorg A. Angehrn and Charles F. Magnani, discloses a method for using data from a borehole televiewer in an active well to determine fluid properties. This method involves determining the wall effects from the data. Once determined, the wall effects are factored out from the data to determine the fluid properties.

U.S. Pat. No. 3,454,085, titled "Well Installation with Plural Flow Meters", issued to J. H. Bostock relates to a well installation providing fluid flow to the earth surface from one or more earth formations by means of a flow conductor which extends through a well bore. The flow conductor has vertically spaced ports between barriers which close the well bore about the flow conductor between each pair of producing formations. The ports provide communication between the flow conductor and the earth formations. Flow meters mounted on the flow conductor are used to determine the rate of flow of fluid in the flow conductor above or below each port so that the rate of flow of fluids between each producing formation and the flow conductor can be determined.

U.S. Pat. No. 3,511,334, titled "Acoustic Well Logging Tool" issued to Joseph Zemanek, Jr. relates to an acoustic well logging tool using an acoustic transducer similar to that used in the borehole televiewer. The logging tool includes a transducer which is secured to a support member in the tool by means of bonding material covering the active face of the transducer. The bonding material has a flattened outer face opposite the active face of the transducer in order to provide an increased directivity of the survey signal and signal-to-noise ratio.

U.S. Pat. No. 3,603,145, titled "Monitoring Fluids in a Borehole" issued to Billy P. Morris, relates to a method and apparatus for monitoring flow and character of fluids in a borehole penetrating subterranean formations. This method includes transmitting acoustic energy through the fluids between transducers in a down-hole tool and discriminating intelligence bits from the acoustic energy arriving at the transducer serving as receiver. A portion of the acoustic energy is transmitted upstream and a portion of the acoustic energy is transmitted downstream. Intermittent acoustic energy is employed and the intelligence bits are, respectively, the travel time downstream and the travel time upstream. This provides information relating to the difference in the respective travel times and the average travel time of the acoustic energy. The information relating to the difference in travel times is related to velocity of flow of the fluids. The average travel time is related to the density of the fluids. In another method, intermittent or continuous acoustic energy is employed and the intelligence bits are respectively, apparent frequency and amplitude. The apparent frequency affords information as to frequency shift which is related to velocity of fluid flow. The amplitude is related to fluid density.

U.S. Pat. No. 4,215,567, titled "Method and Apparatus for Testing a Production Stream", issued to Richard J. Vlcek relates to a method and apparatus for testing a production stream including oil, water, and gas flowing through a conduit to determine their respective percentages. A sample portion of the production stream is pumped through a sample line into a sample chamber where it is heated. It is then allowed to set for a retention period to substantially separate the sample portion into oil and water layers. Gas that evolves from the sample portion is vented from the chamber. At the end of the retention period, the sample portion is pumped back through the sample line into the conduit. As the sample portion flows through the sample line, the oil and water content of the sample and the volume of the sample are measured to determine the oil and water percentages in the sample portion. Also, the volume of the sample portion is measured as it is pumped through the sample line into the sample chamber. By comparing this volume with the volume of the sample portion pumped back into the conduit, the gas-liquid ratio of the sample portion can be determined.

U.S. Pat. No. 3,776,032, titled "Method and Apparatus for Detecting an Inflow of Fluid into a Well", issued to Charles B. Vogel, relates to a method and apparatus for detecting an inflow of fluid into a well during rotary drilling lo of the well. An inflow of gas is detected by an acoustic detecting device and an inflow of water is detected by resistivity detecting device. The resulting information is transmitted to the surface by pressure pulses produced in the drilling fluid circulated during drilling.

U.S. Pat. No. 4,736,348, titled "Method and Apparatus for Logging the Characteristics of Materials Forming the Walls of a Borehole", issued to Adam Bednarczyk, relates to a borehole televiewer logging tool employing a transducer assembly having a transmitter and a receiver of acoustic energy pulses. These pulses represent reflections of the transmitted acoustic energy pulses from the walls of a borehole through a subsurface formation. The transducer assembly is rotated within the borehole and also advanced along the borehole. The received reflection signals are corrected for amplitude modulation resulting from oblique angles of incidence of the transmitted acoustic energy pulses. This occurs when the logging tool is off-center of the borehole, is in an elliptical borehole, or is tilted from the vertical axis of the borehole. The corrected reflection signals modulate an image display so that the borehole wall characteristics for the full circumference of the borehole wall can be identified.

U.S. Pat. No. 3,246,145, titled "Liquid Density Measurement System for Determination of Oil in Water", issued to Robert A. Higgins, relates to a system for determining the relative density of a liquid. The system includes a test chamber into which the liquid is introduced for testing purposes. A radioactive source is positioned on one aide of the chamber for directing radiation through the liquid in the chamber. A radiation detector is positioned on the other side of the chamber for detecting radiation passing through the liquid in the chamber. At least a portion of the walls of the chamber between the source and the detector are of material relatively transparent to low energy radiation. In this device, the low energy radiation is allowed to pass freely from the source through the liquid and to the detector. An energy discriminator responsive to only a predetermined low energy range is interconnected with the detector. And further, a recorder for recording an indication of the radiation detected within the low energy range is interconnected with the discriminator.

None of the foregoing references provide a method of measuring in situ the oil flow rate and the hydrocarbon gas fluid flow rate in the total fluid flow so as to aid in determining the oil producing rate of the oil bearing formation. There may be several oil producing zones within the subsurface formation or contributors to a flow line, and none of the foregoing references provide for a method for measuring in situ the oil flow rate contribution from each of such zones, or each of the contributing lines, to the total oil flow rate from the well.

SUMMARY OF THE INVENTION

The present invention is a method to identify fluid hydrocarbon flow rates in an oil well or a flow line in which there is a unidirectional fluid flow. This method includes moving an acoustic tool through the fluid line. The acoustic tool transmits acoustic energy into the fluid flow. The acoustic tool is capable of receiving the acoustic energy when it is reflected back from interfaces within the fluid flow. The reflected acoustic energy is transformed into electrical signals. These electrical signals are then rectified to provide rectified electrical signals. The amplitude peaks of the rectified electrical signals are identified. The travel time of the amplitude peaks is determined. The amplitude peaks and the time values are used to determine the liquid hydrocarbon flow and the gaseous hydrocarbon flow in the flow line. In an alternate embodiment, an envelope of the rectified electrical signals is obtained. The amplitude maximums of the envelop of the rectified electrical signals are identified. The approximate travel time value of these amplitude maximums is determined. The amplitude maximums and the time values are used to determine the liquid and the gaseous hydrocarbon flow in the flow line.

The present invention is directed to an acoustic logging method for determining oil flow and hydrocarbon gas flow from an oil producing well or wells that penetrate subsurface formations. In wellbore use, an acoustic logging tool is lowered to a select position within an oil producing well. The acoustic logging tool includes a transducer for transmitting and receiving acoustic energy. The transducer transmits compressional wave acoustic energy in a beam into the fluid flow within the producing well from the subsurface formation to the surface of the earth. The transducer receives reflection signals of compressional waves from oil within the fluid flow flowing past the transducer toward the surface of the earth. Such reflection signals occur due to the acoustic impedance changes at water-oil and oil-gas interfaces within the fluid flow. The entire received reflection signals are recorded as a measure of the fluid flow rate within the producing well at the select position of the transducer. The signals are rectified and the amplitude peaks are identified. The travel time of the amplitude peaks is determined. In an alternate embodiment, the envelop of the rectified signals is mapped and, as with the full wavelet, the travel time of identified amplitude maximums is determined.

In a more specific aspect, the logging tool is moved through the producing well to successively position the transducer above each oil producing zone and below the next higher oil producing zone within the subsurface formation. At each successive positioning of the transducer, compressional wave acoustic energy is transmitted from the transducer in a beam into fluid flow in the producing well. Reflection signals received by the transducer from oil within the fluid flow and occurring due to acoustic impedance changes at oil-water interfaces within the fluid flow are recorded. The composition content, oil, gas and water, are determined at each position. Then the value at each previous position is subtracted from the determined flow rate at a subsequent transducer positioning as a measure of the oil flow rate from the oil producing zone lying immediately below the subsequent transducer positioning. The transducer is rotated about the axis of the producing well during the steps of transmitting compressional wave acoustic energy into the fluid flow and receiving compressional wave reflection signals from oil within the fluid flow.

DESCRIPTION OF THE PREFERRED EMBODIMENT

Logging tools appear in many varieties, from neutron logging tools to gamma ray logging tools to resistivity logging tools etc. It can be said that a sub group of all logging tools is acoustical logging tools. Acoustical logging tools can be further divided into at least two categories. The logging tools which use an envelop signal and logging tools that use a full wavelet signal. The present invention deals with the use of both of these types of acoustic tools. A borehole televiewer is one type of acoustic tool that can be used in practicing the present invention. Previously, only the amplitude of the signal from the borehole televiewer has been used to extract the information relating to fluid flow.

Figure 2:
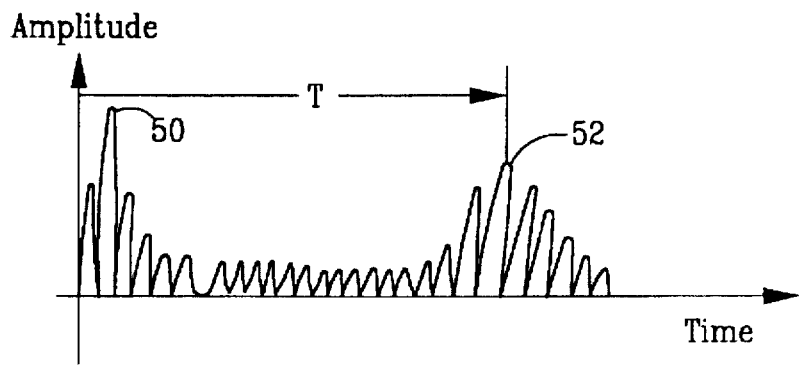
FIG. 2 is an illustration of a full wavelet signal the is typically received in an acoustic transceiver tool.
Figure 6:
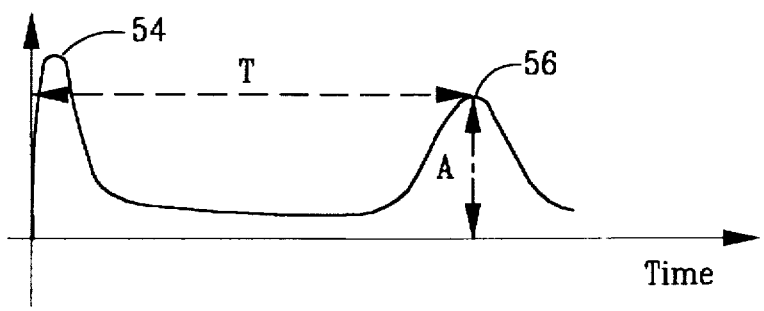
FIG. 6 is an illustration of an envelop signal obtained from the full wavelet signal of FIG. 2.

Regarding the envelop signal and the full wavelet signal, both signals are generated in the same manner. Using the borehole televiewer tool as the acoustical transducer, an acoustical transducer generates 300 kilohertz pressure waves. The pressure wave travels to the borehole wall, is reflected, comes back and is still a 300 kilohertz wave when detected. This type of signal is illustrated in FIG. 2. This type of signal is preferred in surface applications since this signal contains more information and a higher degree of accuracy concerning the quantities that it is used to delineate. Unfortunately this relatively high frequency signal cannot be transferred to the surface in a producing well very easily. What may be done in wellbore applications is to extract the envelop of this signal which is a much lower frequency and transfer it to the surface. At the surface a signal such as that shown in FIG. 6 is received.

In practicing the present invention, the borehole televiewer or similar acoustic device is used to direct a beam of acoustic energy toward the fluid flow in a fluid flow line that may be either a producing oil well or a pipeline. A signal is generated when the reflection of the beam of acoustic energy returns and is detected. The signal is rectified and recorded as a measure of oil flow rate within the line. The amplitude peaks are identified and the travel time of the peaks is determined. The magnitude of this travel time, the time the acoustic wave requires to travel to the casing or conduit and return, is indicative of the magnitude of gas presence in the fluid flow. The shorter the travel time of the amplitude peak of the casing reflection, the less gas present in the fluid flow. The longer the travel time for the amplitude peak from the casing reflection, the more gas present in the fluid flow.

In an alternate embodiment, the signal is rectified and the envelop of the rectified full wavelet of returning signals is taken, reducing the frequency of the signal. The envelop of the reflection signals are recorded as a measure of hydrocarbon flow rate within the well. The amplitude maximums of the envelop are identified and the travel time of the maximum attributed to the casing reflection is determined. The magnitude of this travel time, the time for the reflection of the acoustic wave from the casing or confining conduit, is indicative of the magnitude of gas presence in the fluid flow. The shorter the travel time of the amplitude maximum, the less gas present in the fluid flow. The greater the amount of travel time of the amplitude maximum attributed to the casing or pipeline conduit reflection, the more gas present in the fluid flow.

Figure 1:
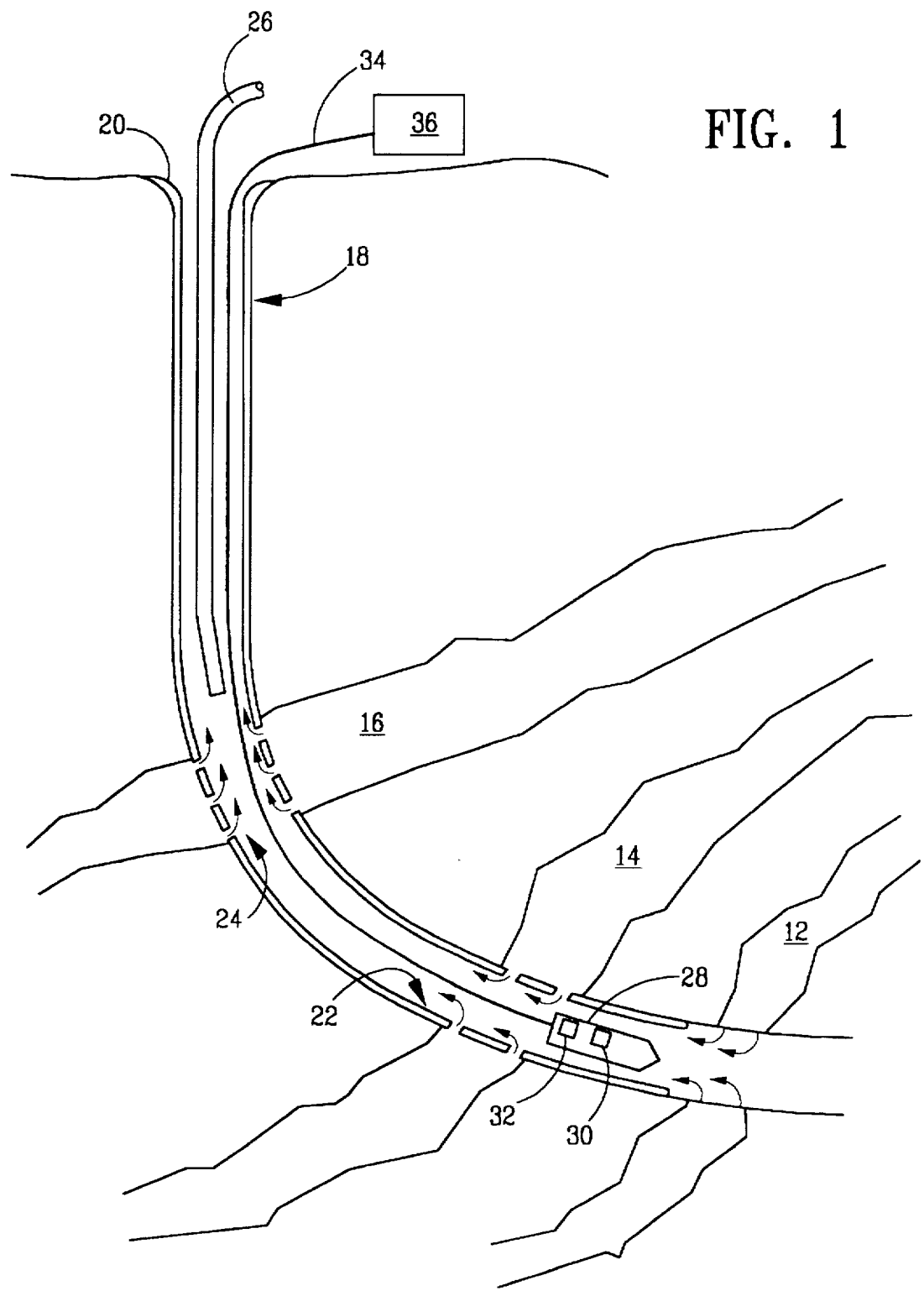
FIG. 1 is a drawing illustrating the positioning of an acoustic logging tool within the horizontal portion of a deviated borehole penetrating a subsurface oil-bearing formation.

In FIG. 1, a deviated wellbore having a generally horizontal section is illustrated. Although a wellbore is shown, the method and apparatus of the present invention may be applied not only to a wellbore, but also to a surface flow line where the composition of the fluid flow is required. This may be in a situation where the outputs of several wells are being manifolded together for transport to a common storage tank, or to a pipeline for transport to a remote location. In either case, the composition from individual wells or the overall composition of the flow is desired. In any of these situations the method and apparatus of the present invention may be used. A wellbore is illustrated as the most difficult of these situations.

Referring now to FIG. 1, a subsurface formation is illustrated having a plurality of hydrocarbon producing zones 12, 14 and 16 and is penetrated by a borehole 18. Casing 20 of borehole 18 is perforated at locations 22 and 24, adjacent each of the hydrocarbon producing zones 14 and 16, respectively, to establish fluid flow from such producing zones into borehole 18 as illustrated by arrows. Such fluid flow, oil, water and gas combined, flows through the well bore and exits by way of a conduit 26.

To monitor the oil flow rate in-situ from each of the producing zones in accordance with the present invention, an acoustic logging tool 28, preferably a borehole televiewer, is lowered down borehole 18. Ideally, acoustic logging tool 28 is lowered to a position immediately above producing zone 12 and below perforations 22 along the next higher producing zone 14. Logging tool 28 includes a transducer 30 for transmitting and receiving acoustic energy.

Transducer 30 transmits a beam of compressional wave acoustic energy into the upward fluid flow from the producing zone 12. As the beam of acoustic energy enters the fluid flow, it is reflected back toward transducer 30 by acoustic impedance changes at oil-water interfaces within the fluid flow. The transmitted beam of compressional wave acoustic energy is reflected from the surface of an oil or water droplet back toward the transducer 30 as a reflection signal illustrated in FIG. 2. Transducer 30 provides the received reflection signal to electronics 32 where it is rectified. In the illustrated embodiment of the present invention, the envelop of the signal is obtained due to the distance it must be transmitted uphole, although the rectified raw signal is preferred since it contains much more detailed information regarding the fluid flow than the envelop signal. The envelop signal is transmitted uphole over logging cable 34 to suitable surface electronics 36 where the amplitudes of the envelop of the reflection signals are recorded in correlation with depth.

Acoustic logging tool 28 may then be moved up wellbore 28 to position transducer 30 at a second selected position above the perforations 22 along the producing zone 14 and below the perforations 20 along the next higher producing zone 12. At this position, transducer 30 transmits a beam of compressional wave acoustic energy into the fluid flow through the producing well. At this position the fluid flow is the combined fluid flows from oil-producing zones 12 and 14. Similar to the first positioning of acoustic logging tool 28, reflection signals are received by transducer 30 from oil and water in the fluid flow and the travel time of these reflection signals is affected both in amplitude and time delay. Transducer 30 provides the received reflection signal to electronics 32 where it is rectified and its envelop signal is obtained. The envelop signal is transmitted uphole over logging cable 34 to suitable surface electronics 36 where the amplitudes of the envelop of the reflection signals are recorded in correlation with depth. This process may be repeated above various producing zones throughout wellbore 18. The combined oil flow rates determined for producing zones below the zone being logged may be subtracted from the flow rate determined at the zone being logged to determine the oil flow rate from only that zone.

As stated previously, both the envelop signal and the full wavelet signal are generated in the same manner. An acoustical transducer generates 300 kilohertz pressure waves. The pressure wave travels to the conduit wall, whether a cased wellbore or a flow line transporting the fluid to a different location. At this conduit wall, the pressure wave is reflected, returns to the transducer and is detected as a 300 kilohertz wave. Also as stated previously, this type of signal is illustrated in FIG. 2. In applications where the envelop of this signal is extracted, a signal such as that shown in FIG. 6 is received. FIG. 6 illustrates the envelop of the rectified signal illustrated in FIG. 2. The full wavelet signal of FIG. 2 is illustrated as having two amplitude peaks 50 and 52, representing a primary reflection and an echo or casing reflection. The envelop signal illustrated in FIG. 6 has maximums designated as maximum 54 and maximum 56. Maximums 54 and 56 correspond to amplitude peaks 50 and 52 of FIG. 2, respectively.

Figure 3:
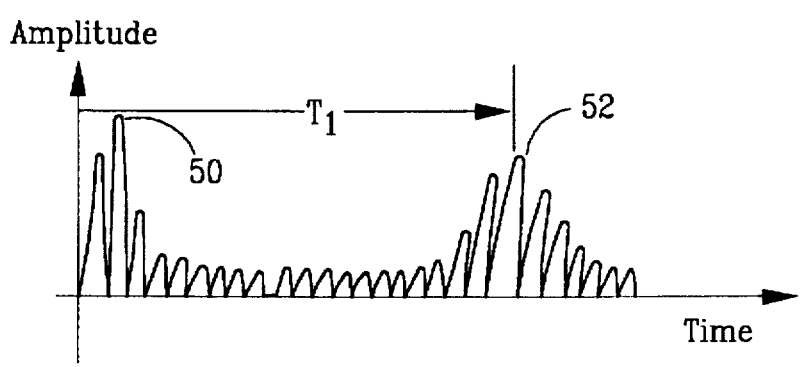
FIG. 3 is a graphical drawing illustrating the waveform received from acoustic energy compressional wave reflections from acoustic impedance changes in the fluid flow in the flow line of FIG. 1 with low gas holdup.
Figure 4:
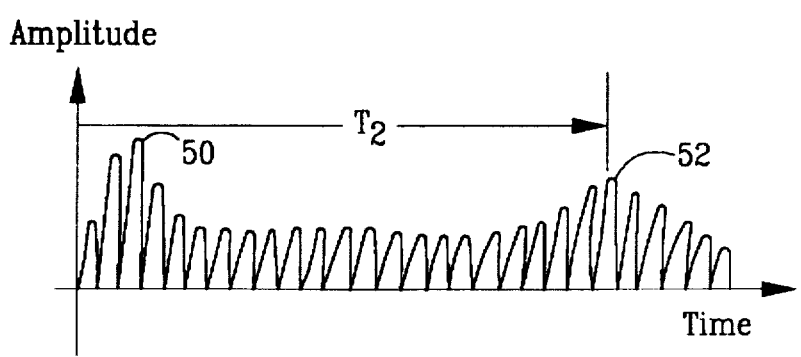
FIG. 4 is a graphical drawing illustrating the waveform received from acoustic energy compressional wave reflections from acoustic impedance changes in the fluid flow in the flow line of FIG. 1 with medium gas holdup.
Figure 5:
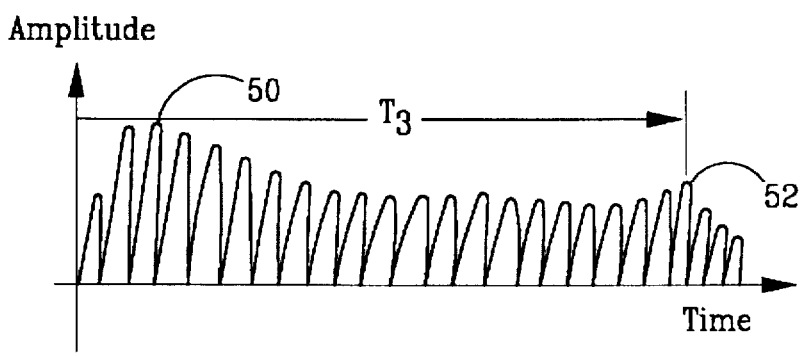
FIG. 5 is a graphical drawing illustrating the waveform received from acoustic energy compressional wave reflections from acoustic impedance changes in the fluid flow in the flow line of FIG. 1 with high gas holdup.
Figure 7:
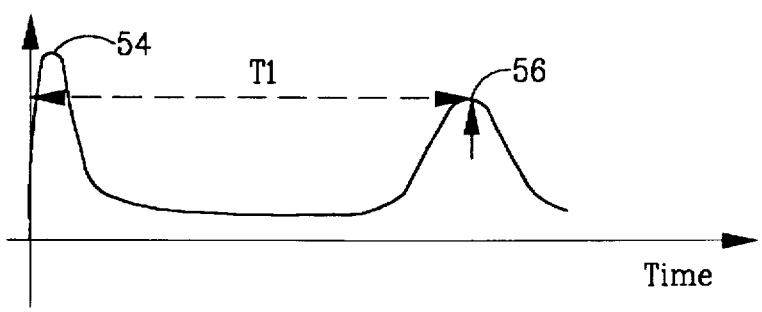
FIG. 7 is an illustration of an envelop signal obtained from the full wavelet signal of FIG. 3.
Figure 8:
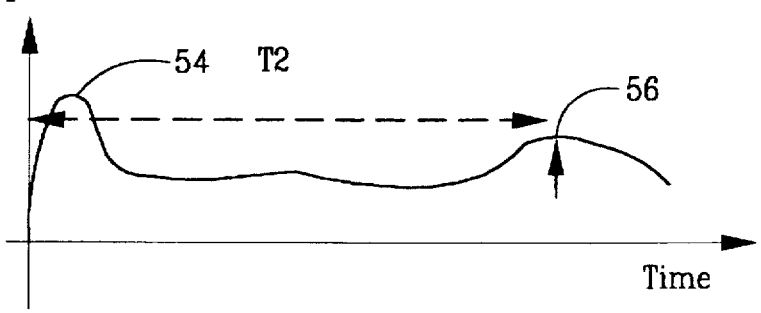
FIG. 8 is an illustration of an envelop signal obtained from the full wavelet signal of FIG. 4.
Figure 9:
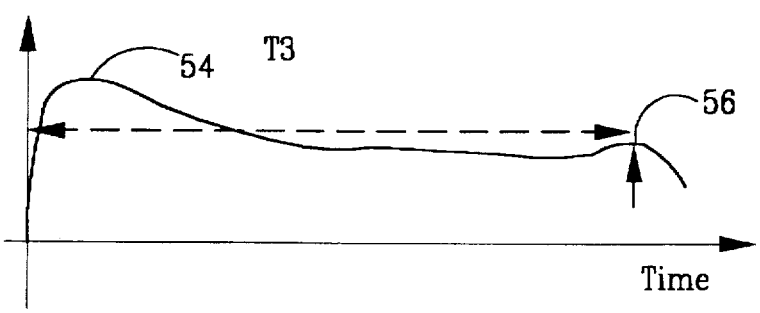
FIG. 9 is an illustration of an envelop signal obtained from the full wavelet signal of FIG. 5.

The full wavelet signal is affected by gas content in the fluid flow as illustrated in FIGS. 3-5. This type of signal is preferred in surface applications since this signal contains more information and the information has an increased accuracy concerning the quantities that it is used to delineate. Unfortunately this relatively high frequency signal cannot be transferred to the surface in a producing well very easily. What may be done in wellbore applications, as previously described, is to extract the envelop of this signal and transfer it to the surface. The envelop of the full wavelet signal is a much lower frequency and is less subject to distortion when transmitted great distances. At the surface a signal such as that shown in FIG. 6 is received. The effects of gas content in the fluid flow on the reflection signals is illustrated in FIGS. 7-9, which approximately correspond to the rectified full wavelet illustrations of FIGS. 3-5, respectively.

FIGS. 2-9 illustrate the full wavelet of the signal and the envelop of the full wavelet of the rectified signal as generally having two amplitude peaks 50 and 52 representing a primary reflection and an echo or casing reflection.

In each of the illustrations in FIGS. 2-5 and FIGS. 6-9, 9 two amplitude peaks or amplitude maximums are identified. The two amplitude peaks are identified as peaks 50 and 52 in FIGS. 2-5. The two amplitude maximums are identified as maximums 25 and 56 in FIGS. 6-9. The time delay for the occurrence of peak 52 and the time delay for the occurrence for maximum 56 are determined in the time axis.

The more gas present in the fluid stream, the weaker the casing reflection is going to be. Also, the bubbles of gas in the fluid stream are going to reflect some energy. This energy is going to arrive at the transducer early in time and delay the arrival of the echo or casing reflection. It is the increase in time delay from time zero to the reflection from the casing or conduit of a pipeline that provides the indication of gas content in the fluid stream.

Referring now to FIGS. 3, 4 and 5 and to FIGS. 7, 8 and 9 experimental data is illustrated that demonstrates this concept of no gas flow, medium gas flow, heavy gas flow. As illustrated, the amplitude peak of the casing reflection, peak 52, is reduced, along with being delayed, from FIG. 3 to FIG. 5. In the envelop illustrations, maximum 56, the maximum caused by the reflection from the casing or pipeline conduit, is reduced, along with being delayed, from FIG. 7 to FIG. 9. This reduction in amplitude and delay of the echo reflection is due to bubble energy, the energy dissipated in encountering gas bubbles in the fluid flow.

FIGS. 3 and 7 illustrate a situation with no or almost no gas holdup. FIG. 3 for the rectified full wavelet waveform and FIG. 7 for the envelop of the rectified full wavelet waveform. The time delay for amplitude peak 52 in FIG. 3 and for amplitude maximum 56 in FIG. 7 is $T_1$.

FIG. 4 illustrates the approximate rectified full wavelet waveform for a situation where medium gas holdup occurs. It is to be noted that in this situation the echo or casing reflection is diminished, along with being delayed, while reflections from the interfaces of density change for gas bubbles increases. In this example the time delay has increased to $T_2$, an approximate ten percent increase over time delay $T_1$, of FIG. 3, with zero or almost no gas holdup, indicating a greater gas content in the fluid flow. While ten percent has been illustrated for example purposes, it is to be understood that the time delay will vary depending upon the gas content in the fluid flow stream.

Similarly, FIG. 8 illustrates the envelop of the approximate rectified full wavelet waveform of FIG. 4 for a situation where medium gas holdup occurs. It is to be noted that in this situation the envelop of the echo or casing reflection is also diminished, along with being delayed, while the envelop of reflections from the interfaces of density change for gas bubbles increases. Thus, the time delay $T_2$, the indication of gas content in FIG. 8, increases over the time delay $T_1$ of FIG. 4, indicating a greater gas content in the fluid flow.

FIG. 5 illustrates the approximate rectified full wavelet waveform for a situation where high gas holdup occurs. In this situation the echo or casing reflection, represented by amplitude peak 52 is diminished to the point of only slightly greater than the reflections from the interfaces of density change for gas bubbles in the previous time period. However, amplitude peak 52 is still discernable for determining the time delay $T_3$ in FIG. 5. Thus, the time delay $T_3$, the indication of gas content in a high gas holdup situation, increases to a significantly greater value than $T_1$, of FIG. 3, the situation with zero or almost no gas holdup, indicating a greater gas content in the fluid flow.

Referring now to FIG. 9, the envelop of the approximate rectified full wavelet waveform of FIG. 5 is illustrated for a situation where high gas holdup occurs. In this situation the envelop of the casing reflection, or amplitude maximum 56 is diminished to the point of only slightly greater than the envelop of the reflections from the interfaces of density change for gas bubbles, along with being further delayed. However, maximum 56 is still identifiable and time $T_3$, can still be determined, although not as easily as in the full wavelet example of FIG. 5. As in the case of the full wavelet, time delay $T_3$ is significantly greater than the time delay $T_1$, of FIG. 6 for the situation with zero or almost no gas holdup, indicating an even greater gas content in the fluid flow than that of $T_2$ of FIG. 8, the situation of medium gas holdup. This time delay is approximately the same as the time delay in the rectified full wavelet illustration.

The present invention provides a method by which a beam of acoustic energy is directed by an acoustic energy transducer toward the fluid flow through the producing well. Full wavelet acoustic energy signals returning to the transducer are recorded and sent uphole. The full wavelet acoustic energy signals are due to the presence of oil-water interfaces within the fluid flow. These signals are reflected by the interfaces and are indications of the presence of oil within the fluid flow. The absence of signals represent the presence of gas in the fluid flow.

Using the method and apparatus of the present invention, amplitude and time are measured from the echo or casing reflection, while previously, only the amplitude was used to determine what the volume of the minor phase is. Better and more accurate results are obtained using the time and amplitude method of the present invention.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

We claim:

1. A method to identify fluid hydrocarbon flow rates in a fluid flow line having a multi-phase fluid flow comprising the steps of:

moving an acoustic tool through the flow line;

transmitting acoustic energy into the fluid flow toward the flow line wall;

receiving said acoustic energy when it is reflected back from the flow line wall and interfaces within said fluid flow;

transforming said reflected acoustic energy into electrical signals;

rectifying said electrical signals;

identifying amplitude peaks of said rectified electrical signals;

determining the return time of said amplitude peaks; and using said amplitude peaks and said return time values to distinguish gas flow and liquid flow in the hydrocarbon fluid flow in the flow line.

2. The method according to claim 1 wherein said step of identifying includes the step of:

selecting amplitude peaks representing a primary reflection and an echo reflection.

3. The method according to claim 2 wherein said step of selecting includes the step of locating a casing reflection.

4. The method according to claim 1 also including the step of:

recording said rectified reflection signals.

5. The method according to claim 4 also including the step of:

determining total fluid flow from said recorded rectified reflection signals.

6. An apparatus for measuring fluid flow in a multi-phase flow line comprising:

means for directing a beam of acoustic energy toward the flow line wall into the fluid flow;

means for receiving reflection signals of said beam of acoustic energy;

means for rectifying said reflection signals;

means for determining an envelop of said rectified reflection signals of said beam of acoustic energy and peaks of said envelop as a measure of flow rate within the flow line; and means for measuring the travel time of said peaks of said envelop to determine gas content of said fluid flow.

7. The apparatus according to claim 6 also including:

means for recording said envelop of said reflection signals.

8. The apparatus according to claim 6 wherein said means for determining an envelop includes:

means for identifying amplitude maximums representing a primary reflection and an echo reflection; and means for locating said echo reflection amplitude maximum.

9. The apparatus according to claim 8 wherein said means for locating said echo reflection includes means for determining a casing reflection.

10. The apparatus according to claim 6 also including:

means for recording said rectified reflection signals.

11. The apparatus according to claim 10 also including:

means for determining total fluid flow from said recorded rectified reflection signals.

12. A method for measuring fluid flow in a multi-phase fluid flow line comprising the steps of:

directing a beam of acoustic energy toward the flow line wall into the fluid flow;

receiving reflection signals of said beam of acoustic energy;

determining an envelop of said reflected signals of said beam of acoustic energy;

identifying an amplitude maximum of said envelop of said reflected signals; and measuring the travel time of said reflected signals to determine gas content of said fluid flow.

13. The method according to claim 12 wherein said step of determining includes the steps of:

identifying amplitude maximums representing a primary reflection and an echo reflection; and locating the travel time position of said echo reflection amplitude peak.

14. The method according to claim 13 wherein said step of locating said travel time position includes the step of determining a casing reflection.

15. The method according to claim 12 also includes the step of:

recording said envelop of said rectified reflection signals.

16. The method according to claim 15 also includes the step of:

determining total fluid flow from said recorded envelop of said rectified reflection signals.

17. A method for determining the liquid and the gaseous hydrocarbon flow rates in a multi-phase fluid flow stream in a flow line comprising the steps of:

placing an acoustic tool in the multi-phase fluid flow stream;

directing a beam of acoustic energy toward the flow line wall into the fluid flow;

receiving said beam of acoustic energy when it reflects back to said acoustic tool;

transforming said reflected beam of acoustic energy into electrical signals;

mapping the envelop of said electrical signals;

identifying amplitude maximums of said envelop of said electrical signals;

determining elapsed time of said maximums of said envelop of said electrical signals; and obtaining the flow rate of gaseous hydrocarbons from said elapsed time of said amplitude maximums of said envelop of said electrical signals.

* * * * *